(12) United States Patent
Lehman

(10) Patent No.: US 6,466,314 B1
(45) Date of Patent: Oct. 15, 2002

(54) RETICLE DESIGN INSPECTION SYSTEM

(75) Inventor: Yonatan Lehman, Moshav Bet Gamliel (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/156,572

(22) Filed: Sep. 17, 1998

(51) Int. Cl.$^7$ ................................................ G01N 21/00
(52) U.S. Cl. ................................. 356/237.1; 356/237.3; 356/237.4; 356/394
(58) Field of Search ........................... 356/237.1, 237.3, 356/237.4, 237.5, 390, 391, 392, 393, 394; 250/548, 561; 382/1, 8; 982/145

(56) References Cited

U.S. PATENT DOCUMENTS

| | | | | |
|---|---|---|---|---|
| 4,641,353 A | * | 2/1987 | Kobayashi | 356/390 |
| 4,701,859 A | * | 10/1987 | Matsuyama et al. | 356/394 |
| 4,718,767 A | * | 1/1988 | Hazama | 356/394 |
| 5,563,702 A | * | 10/1996 | Emery et al. | 356/237.1 |
| 5,767,974 A | * | 6/1998 | Higashiguchi et al. | 356/394 |
| 5,850,467 A | * | 12/1998 | Matsui et al. | 382/145 |
| 5,995,219 A | * | 11/1999 | Tabata | 356/237.5 |

* cited by examiner

Primary Examiner—Frank G. Font
Assistant Examiner—Sang H. Nguyen
(74) Attorney, Agent, or Firm—Sughrue Mion Zinn Macpeak and Seas LLP

(57) ABSTRACT

A method of reticle inspection, comprising generating a test reticle comprising a plurality of test pattern-features thereon; manufacturing a wafer using the reticle; and determining a transfer of at least one of said plurality of pattern features from said reticle to said wafer. Preferably, a neural network is trained using the determination. Preferably, a reticle is inspected by running detected defects through the neural network to determine if the detected defect has a consequence.

4 Claims, 5 Drawing Sheets

RETICLE DESIGN INSPECTION SYSTEM

FIELD OF THE INVENTION

The present invention relates to visual inspection of reticles.

BACKGROUND OF THE INVENTION

Electronic wafers are usually manufactured using a layer-by-layer methodology, with each layer's manufacture including various etching and deposition processes, which are applied with the aid of a reticle and/or a mask. To create a complete layout on a wafer, the reticle is stepped sequentially over the wafer and at each step, the pattern of the reticle is transferred to the wafer.

The reticle itself is the end product of a complicated design process in which the entire layout of the wafer is determined and tolerances are set for the manufacture process. Nevertheless, it is often the case that the final manufactured wafer deviates from the design of the reticle. The reasons for the wafer being different from the design of the reticle may include defects in the reticle manufacture and unexpected interactions between the reticle design and the process used for the wafer manufacture. Therefore, reticles are typically inspected both by the mask shop manufacturing the reticle and at the semiconductor fabrication plant (Fab). According to current practice, reticles having non-repairable defects thereon are not shipped by the mask shop or are returned by the Fab, and never used. Due to the rapid reduction in design rules (the smallest resolvable feature size), manufacturing reticles is expected to become more difficult and the price of reticles is expected to rise. Therefore, it will become more desirable to use a reticle even if it has defects in its manufacture, providing however, that such defects do not invalidate the manufactured wafer.

One method of determining which defects cause problems in wafer manufacture is to simulate the physical processes which are involved in wafer manufacture. When a reticle is inspected after its manufacture, any detected defects are analyzed based on these simulations to determine if they will have an adverse effect on the wafer manufacture. If the adverse effect is within certain tolerances, the reticle is accepted. These simulations may also be used to generate a set of rules that govern which defects in a reticle are acceptable and which are not.

A critical problem with this approach is that the physical process must be understood in order to be simulated. Specifically, a simulation model of the stepper and fabrication process are first constructed. These models require expertise and knowledge of each stepper-fabrication combination, including, for example, the type of stepper used, the technology used to print the wafer and the development process. A new model may be required for each new combination of stepper, exposure and other processing steps and/or parameters. In some cases, a physical understanding of the parameters of the process are not available. As a result, Fab technicians are often uncomfortable relying on a model instead of on the actual equipment used in the Fab.

SUMMARY OF THE INVENTION

One object of some embodiments of the invention is to provide a method of reticle inspection which takes into account physical processes involved in printing a wafer based on the reticle. Preferably however, a detailed knowledge or analysis of the physical processes is not required.

One aspect of some preferred embodiments of the present invention relates to the generation of a test reticle comprising a plurality of pattern-features, generating a wafer using the reticle and determining which defects in the reticle result in unacceptable defects in the wafer and which do not. Throughout this specification, the term "pattern-features" is a short hand to signify either or both of "design features" and "test defects." Design features relate to features that correlate to the design of the circuitry to be printed. Test defects relates to defects which are intentionally introduced onto the test reticle. Both design features and test defects can be inspected for transferability. For example, design features can be inspected for the quality of their transfer, and test defects can be inspected to check whether they "print" onto the wafer.

In a preferred embodiment of the invention, any defects which transfer from a reticle to the wafer are considered unacceptable. Defects in a reticle which do not transfer to a wafer may be considered acceptable. The determination may be absolute or it may include certain tolerances. Alternatively or additionally, even if the defect have an effect on the wafer layout, such defects are graded responsive to whether or not they affect the functionality of the wafer. Alternatively or additionally to using a test-reticle, the transfer of defects may be manually or automatically identified on existing reticles.

Another aspect of some preferred embodiments of the invention relates to training a neural network with the results of the determination of defect transfer. Preferably, the neural network is then used as part of a reticle inspection process, whereby detected defects on the reticle are analyzed using the neural network to determine if they transfer, as defects, to the manufactured wafer.

Another aspect of some preferred embodiments of the invention is that the entire process of the reticle testing can be done without any in-depth knowledge of the printing, development and/or fabrication processes involved.

A neural network training method, in accordance with a preferred embodiment of the invention comprises designing and manufacturing a test reticle, printing the circuit onto a wafer and checking the generated wafer for defects. The defects in the wafer are then matched to defects in the reticle using the known coordinates of the designed test defects. Additionally, the reticle can be inspected for additional unintended defects and their coordinates can be stored in the system's memory. The wafer is then analyzed to see if the defects transferred as unacceptable defects onto the wafer. In some cases, unacceptability is simply that the defect transferred to the wafer, in other cases, unacceptability may be dependent on the functional effect of the transferred defect. In some cases, a defect for one use, may not be a defect for another, less demanding use. In a preferred embodiment of the invention, the neural network is trained by associating particular defects in the reticle with the acceptability of the resulting wafer.

Preferably, the test reticle used is a specially designed test reticle which contains a variety of predetermined pattern-features, some of which may be defective pattern-features. Additionally, the test reticle preferably includes especially designed defects. Alternatively, reticle-wafer sets that are known to contain defects may be used for training. Preferably, the defects are repeated for various dimensions and/or tolerances of the defect. Alternatively or additionally, the defects are repeated on the reticle so that a statistical evaluation of the defect transfer probability can be obtained. Alternatively or additionally, one or more wafers are generated using a plurality of different reticles and/or a plurality of different focus-exposure settings and/or a plurality of different process parameters, so that such statistics may be determined.

As noted above, in a preferred embodiment of the invention, the test reticle includes both a defected and a defect free example of each of a plurality of pattern features and a plurality of designed defects. Then, when analyzing the exposed wafer, the transfer of the defective patterns may be compared to the transfer of the non-defective patterns. Additionally, the wafer can be inspected according to the coordinates of the designed defects to determine whether they had transferred onto the wafer.

In a preferred embodiment of the invention, a combinatorial set of defect cells is produced, including, feature type, defect type and/or defect features. For example, a defect type "non constant width" may be matched with a feature "1 micron conductor" and a defect feature "variation>10%". Each such cell preferably includes a defected feature-pattern and a defect-free feature pattern. In a preferred embodiment of the invention, a defect cell is not spatially contiguous. In a preferred embodiment of the invention, the defected feature patterns are arranged in order in one part of the reticle and the defect-less feature patterns are arranged in a corresponding order in a different part of the test reticle. When the exposed wafer is inspected, the two types of patterns may be optically scanned serially or in parallel and compared to each other.

In one preferred embodiment of the invention, an independent training procedure and/or test reticle is used for each manufacturing process.

In a preferred embodiment of the invention, defects in the wafer are detected by automated inspection. Preferably, the inspection utilizes an optical or electron microscope. For example, the wafer can be first inspected using Orbot WF 7xx™ series wafer inspection system, available from Applied Materials™ inc. of Santa Clara, Calif. Such an inspection will provide a defect map of suspected locations on the wafer. Preferably, the wafer also undergoes a review to verify that the suspected locations are indeed defective. Such a review can be done using, for example, the SEMVision™ electron beam review station, also available from Applied Materials™. The use of SEMVision™ is highly recommended as it is a deterministic tool that can be used to confirm the output of the Orbot WF™, which is of a statistical nature. Alternatively or additionally, destructive inspection methods, such as cross-section transmission electron microscope (TEM) and focused ion beam (FIB), can be employed.

In a preferred embodiment of the invention, when the neural network is trained, a particular defect is associated with various characteristics of the process for which the mask and/or wafer are used. In one example, the characteristics include the type of etching. In another example the characteristics include the clock speed of the device produced on the wafer.

In a preferred embodiment of the invention a table is maintained in which each defect and variations thereof are associated with a suitability for various uses of a wafer generated from a reticle with that defect.

In a preferred embodiment of the invention, a pattern matching computer utilizing pattern matching software and/or dedicated hardware may be used to perform pattern matching instead of a neural network.

A reticle inspection method in accordance with a preferred embodiment of the invention comprises, generating a reticle, inspecting the reticle for possible defects and analyzing the defects with a trained neural network to determine if the defects transfer and affect the manufactured items. Alternatively, the entire reticle may be analyzed, not only suspected defects.

In one embodiment of the invention, the quality of a process is periodically assessed by comparing the defects in resulting wafer with defects in a reticle. Preferably, this assessment may be used to update the training of the neural network.

There is therefore provided in accordance with a preferred embodiment of the invention, a method of reticle inspection, comprising:

generating a test reticle comprising a plurality of test pattern-features thereon;

exposing a wafer using the reticle; and determining transferability of at least one of said plurality of pattern features from said reticle to said wafer.

Preferably, the method comprises training a reticle inspection system to associate a test pattern feature with a consequence of said transfer. Preferably, training comprises training a neural network. Alternatively or additionally, said test reticle does not define an operational layer of an operational integrated circuit. Alternatively or additionally, said pattern feature represents a printing on a reticle which is supposed to meet a design rule and wherein determining a transfer comprises determining if the pattern feature transferred in accordance with the design rule. Preferably, said pattern feature represents a defect in manufacturing a reticle in accordance with said design rule.

In a preferred embodiment of the invention, determining comprises determining a consequence of said transfer. Alternatively or additionally, said plurality of pattern-features comprise optical proximity correction (OPC) patterns. Preferably, said plurality of test pattern features comprises a plurality of pattern features corresponding to a single type of defect at a plurality of degrees of severity. Alternatively or additionally, said plurality of test pattern features comprises a plurality of pattern features corresponding to a plurality of different defect types. Alternatively or additionally, said plurality of test pattern features comprises a plurality of copies of a single pattern feature.

In a preferred embodiment of the invention, the method comprises:

inspecting a manufactured reticle to detect one or more pattern defects; and comparing each of said detected pattern defects to said test pattern-features.

Preferably, the method comprises approving said manufactured reticle if said test pattern feature to which a detected defect is compared, does not transfer.

There is also provided in accordance with a preferred embodiment of the invention, a method of reticle inspection, comprising:

providing a reticle; and matching one or more pattern-features of said reticle to a database of defect pattern-features, each defect pattern-feature associated with a consequence of said defect feature.

Preferably, the method comprises inspecting said reticle to determine one or more possible defects in said reticle, wherein said matching comprises one or more pattern-features which correspond to said possible defects. Preferably, said inspecting comprises comparing said reticle against a design of said reticle.

Alternatively or additionally, said consequence comprises a transfer of a defect onto a wafer manufactured using said reticle. Alternatively or additionally, comprises a non-transfer of said defect. Alternatively or additionally, said consequence comprises an effect on a functionality of a wafer manufactured using said reticle.

In a preferred embodiment of the invention, said matching comprises matching said one or more pattern-features to a database associated with a particular wafer manufacture process. Alternatively or additionally, said matching comprises matching said one or more pattern-features to a database associated with a particular mask manufacture process.

In a preferred embodiment of the invention, said matching comprises matching using a neural network, which database is embodied by said neural network.

There is also provided in accordance with a preferred embodiment of the invention, a production reticle inspection system comprising:

a training engine receiving data of known test defects produced on a test reticle and detected defects found on a test wafer, and providing training results correlating said detected defects to said test defects to identify test defects which have been transferred to the test wafer and test defects which have not been transferred to the test wafer;

an inspection result module receiving manufacturing defects data of defects detected on said production reticle by an inspection system;

a print/no print module receiving the manufacturing defects data and the training results, and providing a defect report identifying which of the manufacturing defects is likely to be transferred to a manufactured wafer.

Preferably, said print/no print module comprises a neural network. Alternatively or additionally, said print/no print module comprises a pattern matching computer.

In a preferred embodiment of the invention, the system includes a re-train feedback loop between a defect review module and said training engine.

There is also provided in accordance with a preferred embodiment of the invention, a test reticle comprising:

a reticle substrate; and a plurality of feature-patterns formed thereon, wherein said plurality of feature-patterns comprises defective feature patterns which may transfer to a manufactured wafer.

Preferably, said defects comprise defects in a reticle generation process.

In a preferred embodiment of the invention, the reticle includes a plurality of optical proximity correction (OPC) feature-patterns.

Alternatively or additionally, said reticle comprises a phase shift mask.

Alternatively or additionally, said defects comprise defects in a wafer manufacture process.

In a preferred embodiment of the invention, feature patterns of said plurality of feature patterns are selected responsive to a particular wafer manufacture process. Alternatively or additionally, feature patterns of said plurality of feature patterns are selected responsive to a particular mask manufacture process. Alternatively or additionally, feature patterns of said plurality of feature patterns comprise a plurality of copies of a single feature pattern. Alternatively or additionally, feature patterns of defect feature patterns comprise a plurality feature patterns, each corresponding to a different defect type. Alternatively or additionally, feature patterns of defect feature patterns comprise a plurality feature patterns, each corresponding to a different severity level for a single defect type.

There is also provided in accordance with a preferred embodiment of the invention, a reticle inspection system, comprising:

a database associating a plurality of feature patterns with a consequence of said feature pattern;

an image input; and a matcher which matches said input image with said database; and a consequence output which outputs a consequence associated with said image input.

Preferably, said database and said matcher are embodied as a neural network. Alternatively or additionally, said consequence comprises a transfer of said feature pattern as a defect, from a reticle to a wafer. Alternatively or additionally, said consequence is associated with a wafer manufacture process definition.

In a preferred embodiment of the invention, the system includes a trainer, which maintains said database. Alternatively or additionally, the trainer generates said database. Alternatively or additionally, the trainer comprises:

a defect image input;

a reference image input; and a database interface which updates said database with a consequence, responsive to one or more differences between said defect image and said reference image.

Preferably, the system comprises a consequence input for entering a consequence. Alternatively or additionally, said consequence comprises an indication if said defect transfers to a wafer or not. Alternatively or additionally, said consequence is associated with one or more wafer manufacturing parameters.

BRIEF DESCRIPTION OF FIGURES

The invention will be more clearly understood by reference to the following description of preferred embodiments thereof in conjunction with the figures, wherein identical structures, elements or parts which appear in more than one figure are labeled with the same numeral in all the figures in which they appear, in which.

DETAILED DESCRIPTION OF THE PREFERRED EMBODIMENTS

Figure 3:
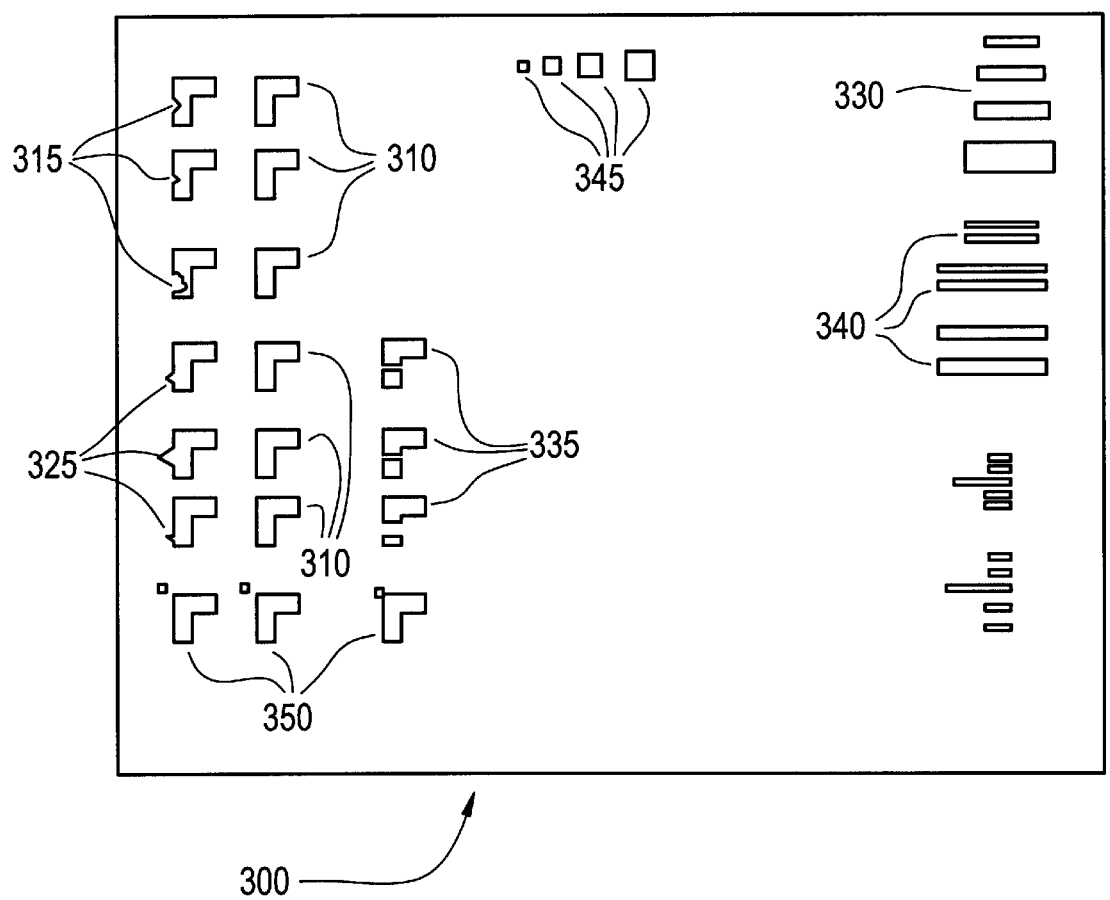
FIG. 3 illustrates a test reticle according to an embodiment of the invention.

In accordance with a preferred embodiment of the invention, a reticle inspection system is trained to recognize which "pattern features" in a reticle transfer to a wafer as unacceptable defects during its manufacture and which do not so transfer. As noted above, the term "pattern-features" is a short hand to signify either or both of "design features" and "test defects." FIG. 3 exemplifies a test mask/reticle substrate 300 which includes both design features and test defects. For example, design feature 310 is a 90° curved conductor line, design feature 320 (not shown) are contact holes of various sizes, design features 330 are isolated lines of various thickness, and design features 340 are grouped lines of various thickness. Similarly, design features 350 are various OPC features. On the other hand, test defects 315 are missing patterns, test defects 325 are extra patterns, test defects 335 are broken contacts of various sizes, and test defects 345 may be either an isolated extra pattern or a simulated foreign particle, such as a dust particle or a pin hole.

Figure 1:
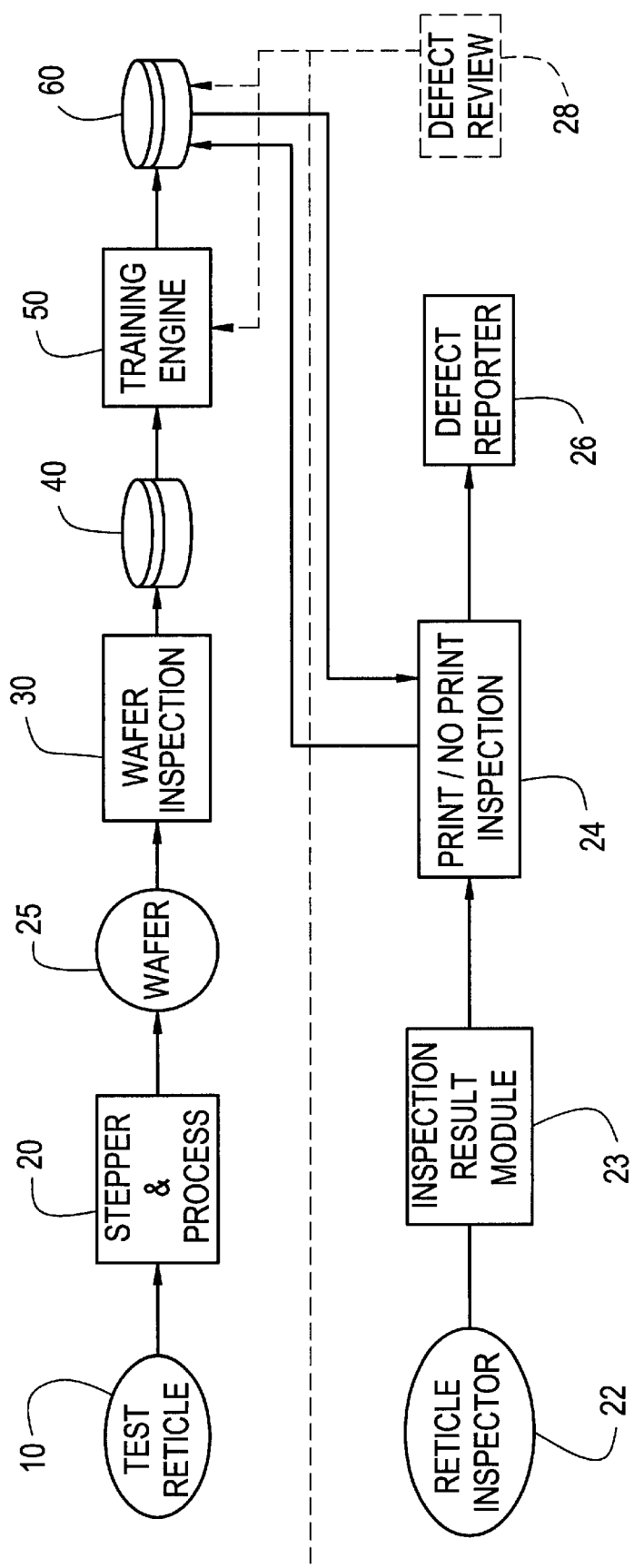
FIG. 1 is a schematic flow diagram illustrating a reticle inspection system, in accordance with a preferred embodiment of the invention.

FIG. 1 schematically illustrates a reticle inspection system, in accordance with a preferred embodiment of the invention. The elements depicted above the dashed line in FIG. 1 relate to the training part of the system, while elements under the dashed line relate to the inspection of reticles by the system.

First, a test reticle is generated (10). The test reticle preferably comprises a plurality of patterns and/or defects, each of which may or may not transfer to the manufactured wafer. Alternatively or additionally, the reticle may include optical proximity correction (OPC) patterns. Alternatively or additionally, the reticle may include other pattern-features, for determining if and how such features transfer from a reticle to a wafer, in various manufacturing settings. These additional pattern-features may include non-defect patterns, for example to be used as a baseline or to test a particular fabrication process (all as exemplified in FIG. 3). The reticle is then preferably used in a stepper to print the circuit on a wafer, and the wafer is developed (20).

The wafer (25) is then inspected for defects (30), to determine for each of the defects in the test reticle whether it passes through to the manufactured mask (or wafer) in an unacceptable manner. In some cases, an unacceptable manner is defined as the situation where a defect transfers to the wafer. In other cases, the unacceptable manner depends of manufacturing tolerances of the fabrication process. Alternatively or additionally, the unacceptable manner is functionally defined, based on the type and/or degree of the effect of the transferred defect on the manufactured wafer. In one example, a transferred defect may limit the usefulness of a wafer to low-power and/or low clock speed operations.

In a preferred embodiment of the invention, the determinations for each pattern-feature are stored in a database 40, where they are preferably used by a training engine 50 to train a neural network 60 (N) with training results. A reticle inspection process, preferably uses these NN results 60 for reticle inspection. Alternatively or additionally to off-line training, the NN may be trained in real-time, as the defects are classified, for example by a human operator.

It should be appreciated that the locations of defects, OPCs and/or other feature-patterns on the test reticle are known, since they were intentionally introduced onto the test reticle. Therefore, it may be sufficient to use a statistical-based wafer inspection system. That is, one may reasonably conclude that if the coordinates of a suspected location output from the wafer inspection system matches the coordinates on the test defect on the test reticle, the suspect location indeed includes a defect. In a preferred embodiment of the invention, only those locations are inspected to see if and/or how the pattern-features transferred. Alternatively or additionally, in some cases only some types of feature patterns and/or some levels of defects will be inspected.

In a preferred embodiment of the invention, a feature pattern with a defect is paired, on the test reticle, with a defect free feature pattern (see, e.g., defect free pattern 310 and defected patterns 315, 325 and 335). Then, in the generated wafer, the images of the defect-free and the defective feature pattern may be compared. Optionally, the pair of feature patterns is relatively positioned in a manner suitable for parallel readout of the two printed features on the using a dual-head optical wafer scanner. Additionally or alternatively, the defective and defect free prints may be electronically tested.

It should be appreciated that there is an interaction between the transfer of the defects and the required process window for manufacturing the production wafer. In the case of some defect types and/or manufacturing parameters, the process window will need to be limited so that a defect in the reticle will not invalidate a wafer. For example, if the defect is a thinning of a conduction line by 10% and the allowed variation is 20%, the process window will need to be stricter so that the non-defect caused variation is under 10%. Another example is a defect in the form of an extra dot near a feature. If the feature is allowed to vary in size by to great an amount, the feature will merge with the dot, possibly invalidating the wafer.

In other defect types and/or manufacturing parameters, the process window may need to be relaxed, so that the defect does not transfer. However, such relaxation usually reduces the total quality of the wafer. In one example, if there is a small gap in a conduction line, allowing the printing to be slightly out of focus will generally smear over the defect. However, if a strict focus is maintained, the gap will print as a gap (see, FIG. 3, patterns 335).

In a preferred embodiment of the invention, training (10, 20, 25, 30, 40, 50, 60) is repeated for different manufacturing circumstances, including, different printing methods and equipment, different wafer fabrication methods and equipment, different stepper types and/or wafer specific information, such as the number of layers underlying the printed layer and/or type of components in—and/or geometry of—overlying or underlying layers. These different circumstances are preferably entered as parametric values (e.g., temperature of etch), so that it is possible to interpolated between two training circumstances. Additionally or alternatively, training is repeated for different usage profiles of the end products. Examples of usage profiles include, reliability requirements (e.g., military standard, Space standard, civilian standard), different manufacturing tolerances and different electronics requirements (e.g., clock speed).

The results of training step 60 are preferably stored in the inspection system, as a pattern database or as a neural network, which will be described in more detail below.

In a preferred embodiment of the invention, alternatively or additionally to training, the results of the defect transfer analysis are used to update principles and parameters for principles which are used for reticle inspection. Preferably, the test reticle is designed to include a plurality of sets of patterns, one set per inspection principle. Alternatively, a single test pattern may be used to update more than one principle. Each set of patterns is preferably used to investigate different values for the parameters of the one principle. Thus, by statistical analysis of the transfer defects from the test patterns it is possible to estimate what values for principle parameters will result in an acceptable wafer. In one example, a principle may be defined as "in 0.5 m wide lines, a variation of up to 0.1 m is allowed." A plurality of test patterns having lines with widths variations of between 0.05 and 0.2 m may be tested. Preferably, all the inspection principles are updated using a test reticle. Alternatively, only inspection principles which are suitable for parameterization are investigated.

As can be appreciated, failures of an end-product integrated circuit may be a result of an error which can be traced back to a reticle. Some of these errors are due to defects in the reticle, some are due to improper mask generation (in manufacturing processes where a mask is used intermediate the reticle and the wafer) and some are due to improper wafer manufacture. These errors may be errors in the transfer of the mask design from one stage to the next, i.e., design to reticle and mask to wafer. Errors in transfer and in wafer manufacture may be caused by faulty processes, for example by a speck of dust on a reticle. However, such errors may also be caused by a defect in the reticle itself, which defect can be detected by inspection. In some cases, the reticle is generated to specification, but these specifications do not correctly take into account process limitations. In some cases, these process limitations may be unknown or imprecisely known. In one example, a certain line spacing may not be attainable in a certain wafer manufacturing process. A reticle which contains such a line spacing for that process is defective, even if it meets its design. Thus, "transfer of defect" means that a defect is apparent in the result, even if such a defect was not apparent in the original. It is important to note that the converse is also possible, i.e., that there may be an error in a reticle (or a mask) but that this error is "corrected" or glossed over by the wafer printing and/or manufacture.

Thus, in a preferred embodiment of the invention, various types of wafer and/or mask inspection methods may be utilized in the training of the inspection system. In a preferred embodiment of the invention, manufactured wafers, test and/or production, are analyzed after they are manufactured, to provide feedback to the reticle inspection system. The analysis may include error classification, whereby errors in the wafer are classified, for example by types, source and/or consequence. Such classification may also be automatic, for example, using a simulation. Additionally or alternatively, the analysis may include wafer inspection, manual and/or automatic.

These testing methods include:

(a) Optical and/or scanning electron microscope inspection.

(b) Destructive testing methods, for example focused ion beam (FIB) cross-section.

(c) Electronic inspection of wafers or component integrated circuits;

(d) Wiring inspection.

(e) Feedback from users.

(f) In-depth analysis of integrated circuit failures.

(g) Simulations.

(h) Environmental testing.

In a preferred embodiment of the invention, the results from these testing methods may be used for correcting design assumptions and process tolerances, in addition to being used for inspection-system training. It should be appreciated that the testing may be performed at a location remote from the reticle manufacturing and inspecting.

FIG. 1 (below the dashed line) also illustrates a method of reticle inspection, in accordance with a preferred embodiment of the invention. First, a manufacturing reticle is inspected by reticle inspector (22) to detect possible defects. This inspection can be performed using Orbot RT 8xxx series reticle inspection tool available from Applied Materials of Santa Clara, Calif. The results of the reticle inspection are inputted into an inspection result module (23) for determination of manufacturing defects data. In one preferred embodiment of the invention, any mismatch between the reticle design and the generated reticle indicates a possible defect. Alternatively or additionally, the reticle is compared to the defect database, possibly without regard to the design requirements, as to whether a feature of the reticle is listed as a possible defect in the training database. Alternatively to matching against the defect database, a rule-based system or a second "possible-defects" database may be used for screening portions of the reticle.

In a preferred embodiment of the invention, the suspected defects are matched against the training defects, to determine which of the possible defects will affect the manufactured wafer (24). Preferably, a defect report is generated which details for each defect whether or not it transfers and/or its effect/non-effect on the manufactured wafer (26).

In a preferred embodiment of the invention, the reticle inspection system comprises a neural network which is trained and is then used to asses the effects of defects. The training set for the neural network preferably comprises a plurality of groups of: (a) design patterns, (b) defects (c) various parameters and (d) whether the defect pattern affects the end-product or not. The various parameters may include the type of process, the required tolerance and other parameters described herein. Alternatively, a separate neural network is maintained for each set of values for the training parameters.

The trained neural network is preferably stored as a list of node weights for each node of the neural network. However, it should be appreciated by those skilled in the art that the neural network can be implemented as an algorithm running on a general purpose computer, a dedicated hardware, or a combination of both. Specifically, hardware modules can be used to expedite section of the algorithm requiring intense calculations.

When a particular type reticle is to be examined, the node weights are loaded into the neural network structure and the reticle or particular features of it are analyzed. In situations where the neural network hangs or provides an otherwise unreliable answer, an operator is preferably notified. Alternatively, the defect is determined as being non-allowable or a commercial simulation tool is being consulted to make a decision.

Figure 4:
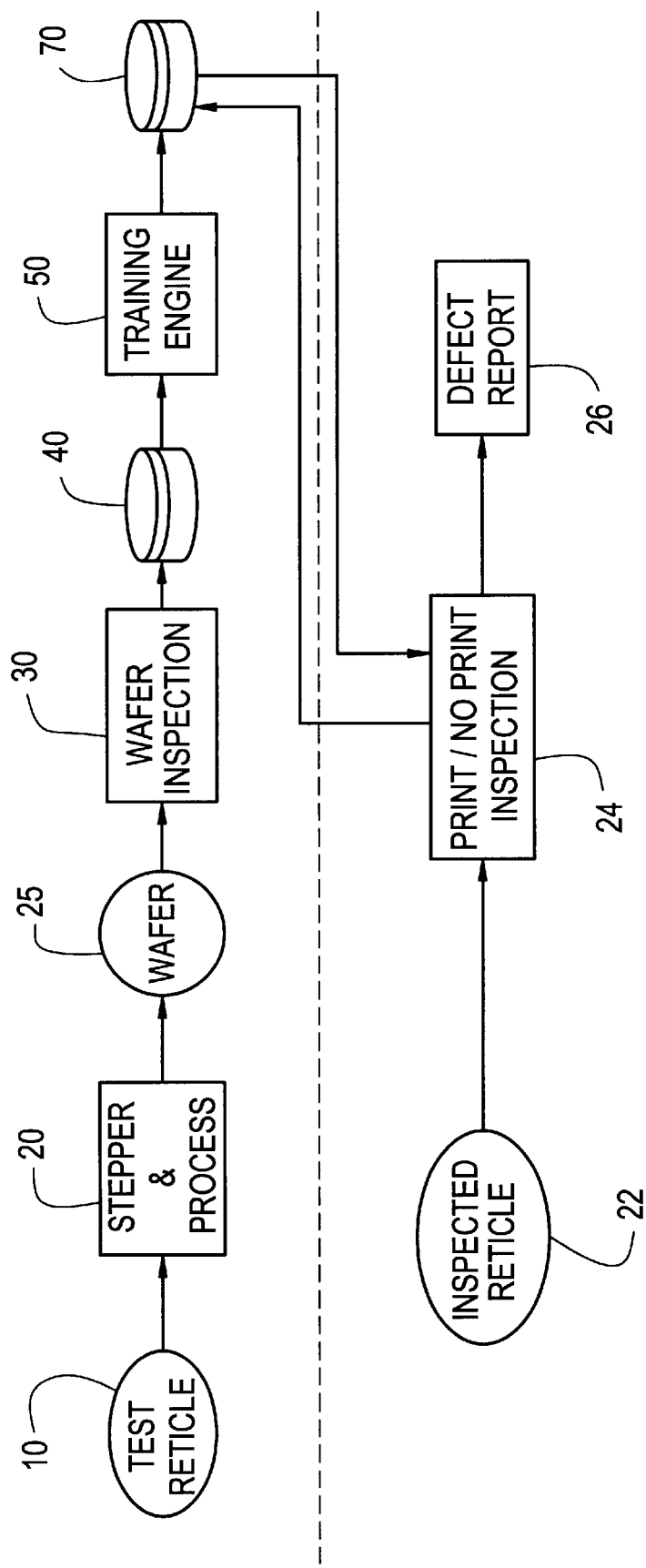
FIG. 4 is a schematic flow diagram illustrating a second embodiment of a reticle inspection system.

In an alternative preferred embodiment of the invention shown in FIG. 4, a pattern recognition mechanism (70) is used instead of a neural network to match a particular reticle feature against a database of defects and their consequences. Preferably, the pattern database is hierarchical so that a database matching does not require matching against all the patterns in the database. It should be appreciated that the classification of defects and/or other feature patterns on the test reticle is generally known beforehand and may be inputted to the training stage. Alternatively or additionally, examples of defects may be developed into rules, for example using data mining techniques for self classification. Preferably, when there are two or more patterns which match, the determined consequence is a weighted average of the stored consequence for each pattern. Alternatively or additionally, a worst case value is used. The pattern recognition mechanism preferably comprises a general purpose computer running pattern recognition software. Alternatively or additionally, dedicated pattern recognition hardware may be used.

In one embodiment of the invention, the inspection process is multi-tiered. In some cases, various defects may be commonly transferable for a group of manufacture situations. The reticle is scanned first for these defects using, for example, Orbot RT 8xxx series reticle inspection tool available from Applied Materials of Santa Clara, Calif. Then only some of the discovered defects, for example small defects or defects which are more individual to the process, can be sent to the inspection process of the invention. Thus, a "filter" can be implemented which sends only certain defects to the print/no print module. Alternatively, suspected defects are compared first to a general database and then to a more specific database. Alternatively or additionally, multi-tiered inspection is used to classify a reticle by quality or by suitability for certain uses.

In a preferred embodiment of the invention, training may continue while the inspection system is in use in the production line, instead of- or in addition to- the training described above. Continuing training is indicated in FIG. 1, by an arrow going from defect review stage 28 to training engine 50 and training results 60. Defect review can be performed using the RT 8xxx at higher magnification or sensitivity, or using another tool, such as the SEMVision described above. It should be noted that a defect review process may uphold or reverse a decision of the inspection system. In one example, a defect review may assert that an indicated defect is not a defect and/or has a different consequence than suggested by the system. In another example, a defect review may assert that a defect or a different type of feature allowed by the inspection system is indeed a defect. In this embodiment, the reticle inspection system is continuously trained with new results of the transferability of defects. Thus, the reticle inspection system can adapt to a particular fabrication plant and/or process. In a preferred embodiment of the invention, the reticle inspection system adapts to changes in the process performance. Alternatively, the reticle inspection system may be retrained periodically to account for changes in the process. Alternatively, the comparison of defects in reticles and wafers may be used for quality control of a particular fabrication plant and/or process.

When training neural networks, a considerable amount of training is required to train the network so that its responses are approximately what is desired. After that, another amount of training is required to make the responses correct. In a preferred embodiment of the invention, the first phase of training is performed using numerical simulation data. Alternatively or additionally, when a process is changed, the starting point for the training is the previous training. Alternatively or additionally, the training for one process is a starting point for the training for a second process.

One aspect of the present invention relates to the selection of patterns to use in a test reticle. In a preferred embodiment of the invention, the following types of patterns are included:

(a) Reticle manufacturing defects, such as wrong spacing, non-constant line width, missing chrome, extra chrome, thin gray and/or isolated defect.

(b) Patterns which are suspected of negatively interacting with the manufacturing processes.

(c) Standard test patterns, which measure resolution, for example, isolated lines and/or line groups.

(d) Test patterns which emulate the finest tolerances required by the manufacturing process.

(e) Test patterns which mimic common patterns in "real" reticles, for example lines, dots, corners and/or line pairs.

(f) Test patterns which mimic difficult patterns in "real" reticles.

(g) Optical Proximity Corrections (OPC), for example over-compensated corners.

(h) Other patterns which may be used to test the suitability of reticle design rules.

(i) Phase shift masks.

In a preferred embodiment of the invention, a multi-dimensional space of defects may be defined, with dimensions including type of defect, severity of defect and/or other parameters of defects. Preferably, each defect (of the defect space), which is implemented on the reticle, is paired with a non-defective feature pattern. Thus, in the generated wafer, it is possible to directly compare the defective and non-defective feature patterns.

In a preferred embodiment of the invention, each test pattern is provided in a plurality of tolerances and/or levels of severity of the defect, so that it is possible to determine for each process which tolerances are met and which are not. Level of severity may include different sizes, geometries and/or distances from desirable features. In one example, patterns may be provided for two lines spaced by $0.5\mu$, $0.4\mu$, $0.3\mu$, $0.2\mu$ and $0.1\mu$. In another example, patterns may be provided for breaks in lines, where the breaks are $0.05\mu$, $0.1\mu$ and $0.2\mu$ is size. In another example, patterns are provided for a 10%, 20%, 30% or 40% variation in line width, for lines of widths $0.2\mu$, $0.3\mu$, $0.4\mu$ and $0.5\mu$. Preferably, when using ranges, the ends of the ranges are also imprinted on the reticle. Thus, the reticle preferably includes patterns which should never cause a defect and patterns which should always cause a defect. These patterns may be used to determine if the test-wafer was manufactured properly.

Additionally or alternatively, in a preferred embodiment of the invention, each pattern is repeated on the reticle a plurality of times. The repetition is useful to determine statistics of failure and/or to better detect defects which have only a low-probability of failure.

In a preferred embodiment of the invention, multiple patterns relating to a single type of defect are distributed or repeated over the entire reticle, so that differences between the defects transferability at different parts of the reticle may be determined. In addition, when testing the wafer generated by the test reticle, the spatial location of the pattern is preferably noted. In many cases, the probability of a defect transferring is dependent the spatial location of the defect relative to the wafer coordinates. In some cases, this may indicate a problem or a characteristic of the step-and-repeat process. For example, a defect may only transfer at the edge of the wafer and not at its center. Thus, the circuits at the center of the wafer are of a higher quality than those at the ends of the wafer.

In a preferred embodiment of the invention, the same test reticle is used for a plurality of processes, potentially yielding different defect transfer data for each process. Alternatively, a test reticle may be customized for a particular process. In a preferred embodiment of the invention, the same test reticle is used while varying different parameters of the process, for example focus and exposure of the stepper. The results of defect transfer may be used to estimate an optimal process parameter set and/or process window. Alternatively, the results can be used to assess which variable of the process is affecting which defect transfer.

Moreover, depending on the symmetry of the reticle, it can be exposed in two or four orientations. That is, if the reticle comprises only one circuit, it can be exposed four times, each time rotating it by 90 degrees. However, if it containes two circuit that are symmetrical over one axis, the wafer can be exposed twice, rotating the reticle 180 degrees in between exposures.

In a preferred embodiment of the invention, a defect has associated therewith a "consequence", which may be more complex than a go/no go indication. In one example, the consequence may be a degradation of the positioning of a layer above the defective layer. In another example the consequence may be a decrease in life expectancy. In a preferred embodiment of the invention, when inspecting a reticle, a set of requirements is provided and the system indicates which of the requirements are met, which are not, probabilities of defect transfer and/or approximate level reliability.

Figure 2:
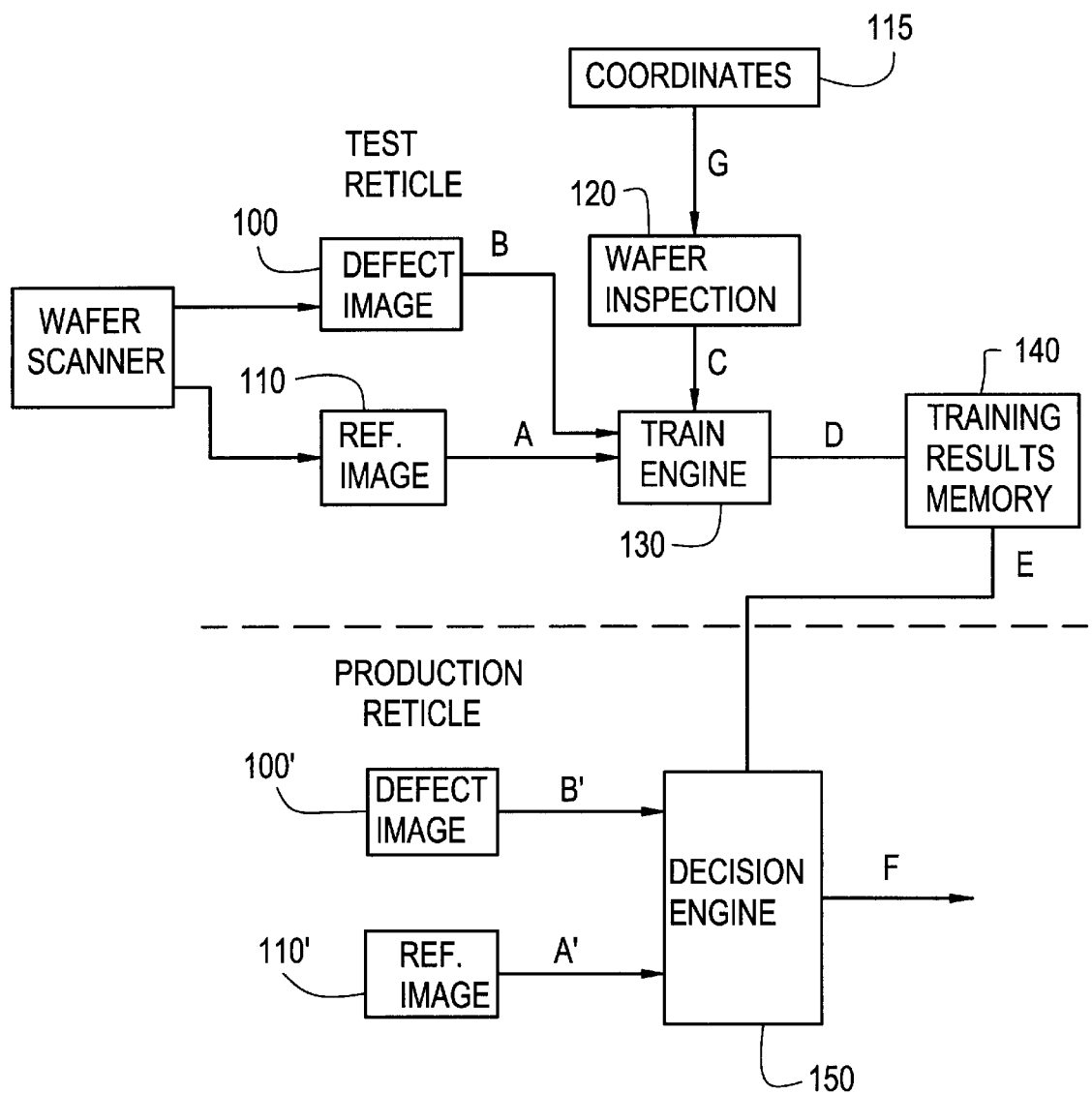
FIG. 2 illustrates an implementation of a method of reticle inspection, in accordance with a preferred embodiment of the invention.

FIG. 2 schematically illustrates an implementation of a preferred embodiment of the invention. Again, elements above a dashed line relate to a test reticle and training engine, and elements below the line relate to inspection of production reticles. First, a test reticle is prepared, for example as described above. A pair of images, including a defect image 100 and a defect free reference image 110, are preferably obtained from the test reticle by a wafer scanner 155 and are sent to the training engine 130 (indicated as arrows A and B). The reference image preferably includes a portion of the reticle in which the pattern having the defect is repeated, sans the defect. Each image preferably includes reticle coordinates at which the images were obtained, so that the defect itself can be identified.

The test reticle is used to expose a wafer, which is then placed in a wafer inspection station 120. The coordinates, 115, of images 100 and 110 are fed into station 120 (arrow G), which checks for each pair to see if the defect printed. The results are preferably fed to a training engine 130 (indicated by an arrow C). Training engine stores the results of the analysis of station 120 in a memory 140, preferably a neural network. As can be appreciated, a different training method may be used, for example a look-up table and/or a pattern matching engine. In a preferred embodiment of the invention, the look up table may be Result="A"+"B", where "+" indicates a concatenation operator. Alternatively, the look-up table includes only defect image 100, and an indication of whether or not it is permissible.

Once memory 140 is sufficiently trained, inspection of production reticles can commence. For each defect two images are provided, an image 100' of the defect and a reference image 110'. The reference image may be an image from an adjacent die or an image from the reticle design database. Alternatively or additionally, it may be a representation of what is defined by the design rule. These images are fed into a decision engine 150, to determine (F), using memory 140, whether the discovered defect will print on a production wafer. Alternatively or additionally to using two images, the defect image may be provided to engine 150, along with an indication of the original design.

Figure 5:
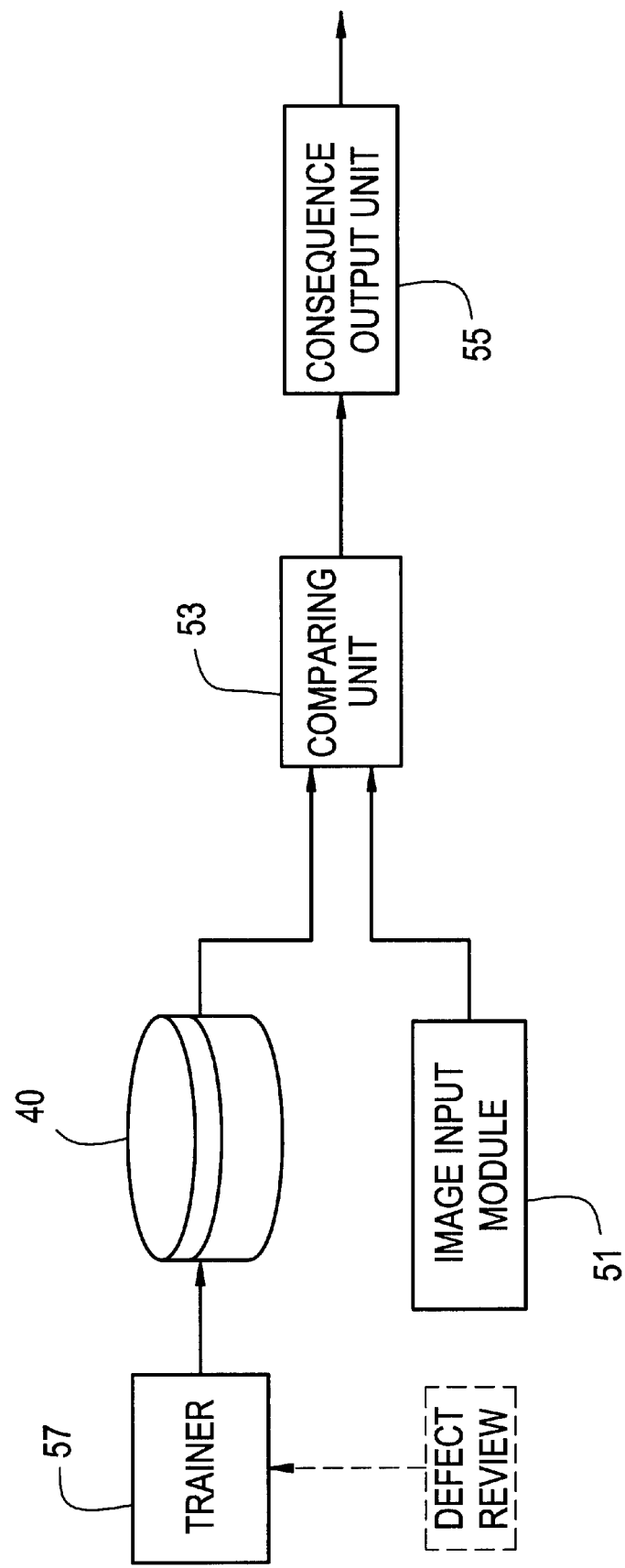
FIG. 5 illustrates a reticle inspection system according to an embodiment of the invention.

FIG. 5 schematically illustrates a reticle inspection system according to a preferred embodiment of the invention having a database 40 associating a plurality of feature patterns of a reticle with a consequence of transferring the feature pattern to a wafer. An image input module 51 outputs a signal to a comparing unit 53 which compares the input image with an input from the database. A consequence output unit 55 receives an input from the comparing unit and outputs an image quality of said image input based on results of the comparing unit. A trainer 57 may continue training the database while the inspection system is in use in response to an input from a defect review stage 28.

It will be appreciated that the above described methods of reticle inspect and reticle inspection system training may be varied in many ways, including, changing the order of steps, which steps are performed on-line or off-line and the exact implementation used, which can include various hardware and software combinations.

It will be appreciated by a person skilled in the art that the present invention is not limited by what has thus far been described. Rather, the scope of the present invention is limited only by the following claims.

What is claimed is:

1. A reticle inspection system comprising:

a training engine receiving data of known test defects produced on a test reticle and data of defects detected on a test wafer, and outputting training results correlating said defects detected on said test wafer to said test defects, thereby identifying test defects which have been transferred to the test wafer and test defects which have not been transferred to the test wafer;

an inspection result module receiving manufacturing defect data of defects detected on a production reticle by an inspection system;

a print/no print module receiving an input from said inspection result module and the training results, and a defect reporter which receives an input from said print/no print module and identifies which of the manufacturing defects is transferred to a manufactured wafer.

2. A system according to claim 1, further comprising a neural network.

3. A system according to claim 1, further comprising a pattern matching computer.

4. The reticle inspection system of claim 1, further comprising a defect review stage and a re-train feedback loop connected between said defect review stage and said training engine.

* * * * *